United States Patent
Duffy et al.

(10) Patent No.: US 7,108,682 B2
(45) Date of Patent: Sep. 19, 2006

(54) DEVICE FOR PROTECTING A DISTAL PORTION OF A CATHETER SYSTEM DURING SHIPMENT AND STORAGE

(75) Inventors: Niall Duffy, Galway (IE); Ronan Thornton, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 701 days.

(21) Appl. No.: 10/350,906

(22) Filed: Jan. 24, 2003

(65) Prior Publication Data

US 2004/0147880 A1    Jul. 29, 2004

(51) Int. Cl.
    *A61M 5/00*    (2006.01)
(52) U.S. Cl. ...................................... 604/263
(58) Field of Classification Search ................ 604/192, 604/198, 263, 164.08, 171, 172; 206/438, 206/363
    See application file for complete search history.

(56) References Cited

U.S. PATENT DOCUMENTS

| 991,015 | A | * | 5/1911 | Payne | 604/263 |
|---|---|---|---|---|---|
| 2,857,912 | A | * | 10/1958 | Feinstone et al. | 604/192 |
| 3,169,527 | A | * | 2/1965 | Sheridan | 604/172 |
| 3,439,675 | A | * | 4/1969 | Martin | 604/192 |
| 3,633,758 | A | * | 1/1972 | Morse et al. | 211/85.13 |
| 3,884,230 | A | * | 5/1975 | Wulff | 604/198 |
| 4,139,009 | A | * | 2/1979 | Alvarez | 604/198 |
| 4,230,115 | A | * | 10/1980 | Walz et al. | 604/517 |
| 4,735,618 | A | * | 4/1988 | Hagen | 604/192 |
| 4,820,277 | A | * | 4/1989 | Norelli | 604/192 |
| 4,887,998 | A | * | 12/1989 | Martin et al. | 604/110 |
| 4,909,792 | A | * | 3/1990 | Norelli | 604/192 |
| 4,921,490 | A | * | 5/1990 | Spier et al. | 604/192 |
| 4,966,591 | A | * | 10/1990 | Yuen | 604/192 |
| 5,092,851 | A | * | 3/1992 | Ragner | 604/192 |
| 5,342,322 | A | * | 8/1994 | Nathan et al. | 604/192 |
| 5,591,134 | A | * | 1/1997 | Shu | 604/192 |
| 6,602,244 | B1 | * | 8/2003 | Kavanagh et al. | 604/544 |
| 6,939,331 | B1 | * | 9/2005 | Ohshima | 604/263 |
| 2002/0130059 | A1 | | 9/2002 | Armijo | |
| 2003/0009191 | A1 | | 1/2003 | Wensel et al. | |
| 2003/0208160 | A1 | * | 11/2003 | Crawford | 604/164.08 |

FOREIGN PATENT DOCUMENTS

DE    296 15 067    3/1998

* cited by examiner

*Primary Examiner*—Sharon Kennedy

(57) ABSTRACT

The present invention protects a distal portion of a catheter during shipment and storage. The device holds the distal portion suspended such that it does not contact the device. The suspended portion is protected from damage resulting from abrasion. When the suspended portion includes a therapeutic coating, the coating is protected from the risk of impaired performance resulting from a therapeutic agent migrating out of the coating and into the packaging material or components of the packaging material migrating into the therapeutic coating, both of which can occur if a therapeutic coating remains in contact with another material for an extended period of time.

26 Claims, 3 Drawing Sheets

DEVICE FOR PROTECTING A DISTAL PORTION OF A CATHETER SYSTEM DURING SHIPMENT AND STORAGE

TECHNICAL FIELD

This invention relates generally to packaging devices for medical catheters. More specifically, the invention relates to a device for protecting a distal portion of a catheter system during shipment and storage.

BACKGROUND OF THE INVENTION

Heart disease, specifically coronary artery disease, is a major cause of death, disability, and healthcare expense in the United States and other industrialized countries. In atherosclerosis, one form of heart disease, deposits of hard plaques (atheromas) may be formed within the inner coat of a vessel (intima) and inner media of arteries. This atherosclerotic disease process leads to a critical narrowing (stenosis) of the affected coronary artery and produces anginal syndromes, known commonly as chest pain. The progression of the narrowing reduces blood flow, triggering the formation of a blood clot (thrombus). The clot may further reduce or entirely prevent the flow of oxygen-rich blood to heart muscles, causing a heart attack. Alternatively, the clot may break off and lodge in the vessel of another organ, such as the brain, resulting in a thrombotic stroke.

One method for treating atherosclerosis and other forms of coronary narrowing is percutaneous transluminal coronary angioplasty (PTCA). During PTCA, commonly a balloon catheter device is inflated within the stenotic vessel. Upon inflation, the pressurized balloon exerts a compressive force on the lesion, thereby increasing the inner diameter of the affected vessel.

Soon after the procedure, however, a significant proportion of treated vessels restenose. To prevent restenosis, a stent may be implanted within the vessel. The stent acts as a scaffold to support the lumen in an open position and maintain lumen size. For insertion, the stent is affixed in a compressed configuration along the delivery catheter, for example crimped onto a balloon that is folded or otherwise wrapped about a guide wire. After the stent is properly positioned within the vessel, it is expanded, causing the length of the stent to contract and the diameter to expand.

Because stent insertion can cause undesirable reactions such as inflammation, infection, thrombosis, or proliferation of cell growth that occludes the passageway, stents are sometimes coated with therapeutic agents to assist in preventing these conditions. The coatings are bioengineered to release precise doses of the therapeutic agent. However, if the coating remains in direct contact with another material for an extended period of time, for example during shipping and storage, the therapeutic agent may migrate into the other material, resulting in delivery of a lower dose of the therapeutic agent than intended. Alternatively, components of the other material may migrate into the therapeutic coating, again leading to impaired performance of the therapeutic agent.

Therefore, it would be desirable to have an improved packaging device for protecting a coated stent affixed to a distal portion of a catheter system that overcomes the aforementioned and other disadvantages.

SUMMARY OF THE INVENTION

The present invention is a device for protecting a distal portion of a catheter system during shipment and storage. The device comprises a catheter tip holding portion to releasably hold a catheter tip and a protective portion operably connected to the catheter tip holding portion. The protective portion suspends and at least partially encloses a distal portion of the catheter system within the device such that the distal portion is protected during shipment and storage. The device may also include a catheter shaft holding portion operably connected to the protective portion. The catheter shaft holding portion releasably holds a portion of a catheter shaft that is proximal and adjacent to the protected portion of the catheter system.

The aforementioned and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
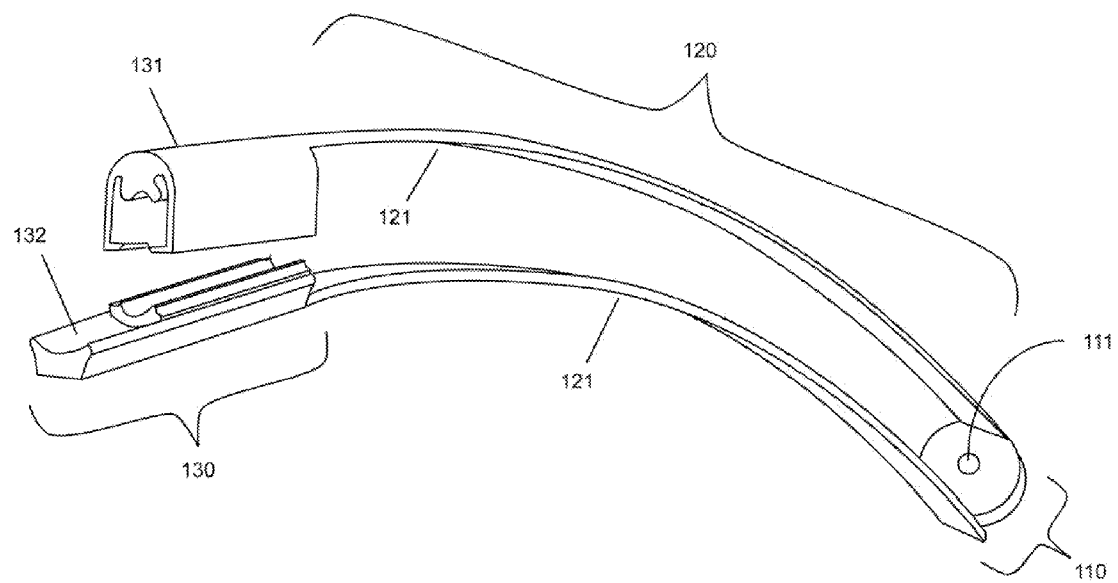
FIG. 1 is an illustration of one embodiment of a device for protecting a distal portion of a catheter system during shipment and storage, in accordance with the present invention.

FIG. 1 illustrates one embodiment of the device for protecting a distal portion of a catheter system, and is generally referred to at 100. Device 100 includes a catheter tip holding portion 110, a protective portion 120, and a catheter shaft holding portion 130. Catheter tip holding portion 110 includes an opening 111 into which a catheter tip is inserted. Protective portion 120 includes two elongate members 121 that extend from the catheter tip holding portion. Catheter shaft holding portion 130 includes two structures 131 and 132 that extend from the two elongate members. Device 100 may have an overall arcuate shape to facilitate insertion of the device and catheter system into a packaging hoop.

Catheter tip holding portion 110 is designed to retain a tip of a catheter, the tip being located at the distal end of the catheter system. The tip may include a stylet, and the stylet may be held by the catheter tip holding portion of the device. Catheter tip holding portion 110 may include an opening 111 into which the catheter tip may be inserted. The opening may be circular or any other shape appropriate for holding the catheter tip. Opening 111 may be sized such that the inner diameter of the opening is approximately the same size as the outer diameter of the catheter tip and such that it holds the catheter tip lightly without inducing deformation of the catheter tip. Opening 111 may also be sized such that it is larger than the catheter tip and may be partially filled or covered with a soft material that provides a high coefficient of friction to aid in holding the catheter tip. For example, a device fabricated using a hard polymer or metal may include a soft polymer within or over the opening to aid in holding the tip.

Protective portion 120 includes two elongate members 121 extending from the catheter tip holding portion. A distal portion of the catheter system, for example a portion bearing a coated stent, is held suspended in air between the two elongate members. The suspended portion of the catheter system may be partially enclosed, as shown in FIG. 1, or may be fully enclosed. If the suspended portion is partially enclosed, the extent of enclosure should be sufficient to protect the suspended portion of the catheter system from contact with its surroundings during shipment and storage.

Catheter shaft holding portion 130 includes two structures 131 and 132 that extend from the two elongate members 121 and releasably hold a portion of a catheter shaft that is proximal and adjacent to the protected portion of the catheter system. The structures 131 and 132 may form a latching mechanism that releasably interlocks, holding the catheter shaft within the latching mechanism. The structures 131 and 132 may also be formed such that they do not latch closed but are designed to interlock by means of compression. The compression may be provided by fabricating the elongate members and catheter shaft holding structures using a shape-memory material that returns the structures to an interlocked position after being opened to insert the catheter system. The compression may also be provided by the user of the device pressing the structures into an interlocked position about the catheter shaft. The structures may be designed such that, when interlocked, they leave an opening sized to releasably hold the catheter shaft without inducing deformation.

Device 100 may be fabricated from one or more suitable materials that can be conventionally formed and processed, for example polypropylene, polyethylene, a nylon/polyethylene blend, polytetrafluoroethylene (PTFE), or a metal. Such materials may minimize exchange of chemical components between the catheter system and the device during shipment and storage. That is, such materials may be non-reactive with a therapeutic agent carried in a stent coating or with other desirable coating materials, thus reducing or eliminating the risk of a therapeutic agent or other coating component migrating out of the coating and into the device material, or of a component of the device material migrating into the therapeutic agent or other coating material. Device 100 may be fabricated using one or more methods such as blow molding, injection molding, stamping, machining, or wire forming.

Figure 2:
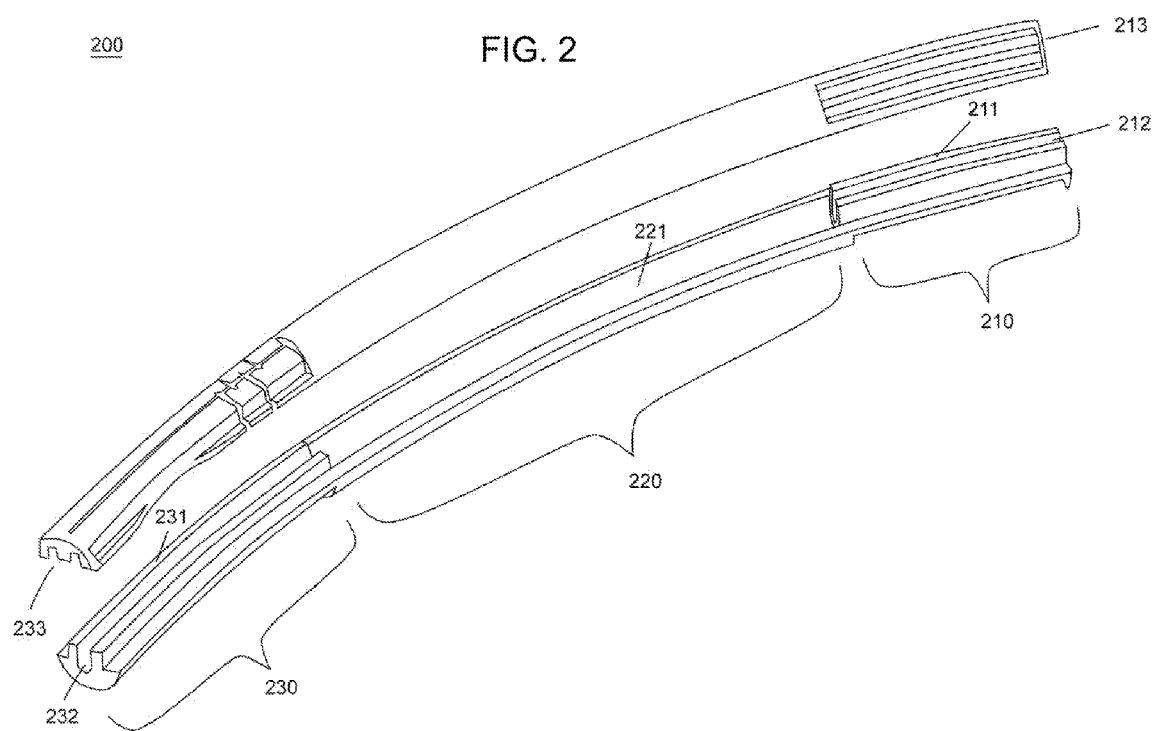
FIG. 2 is an illustration of another embodiment of a device for protecting a distal portion of a catheter system during shipment and storage, in accordance with the present invention.

Another embodiment of the device, in accordance with the present invention, is illustrated in FIG. 2 at 200. Device 200 comprises at least two separable sections and includes a catheter tip holding portion 210, a protective portion 220, and a catheter shaft holding portion 230. Catheter tip holding portion 210 may include a first support member 211, and the support member may include an elongate channel 212. Catheter tip holding portion 210 may also include a latching mechanism 213. Protective portion 220 may include a protective well 221. Catheter shaft holding portion 230 may include a second support member 231, and the support member may include an elongate channel 232. Catheter shaft holding portion may also include a latching mechanism 233. Device 200 may have an overall arcuate shape to facilitate insertion of the device and catheter system into a packaging hoop.

Catheter tip holding portion 210 is designed to releasably hold a catheter tip located at the distal end of the catheter system. The catheter tip may include a stylet, and the stylet may be held by the catheter tip holding portion of the device. Catheter tip holding portion 210 may include one or more support members 211. Each support member may include an elongate channel 212 into which the catheter tip is placed. The channel or channels may be designed such that, when the two separable sections of the device are combined, an opening remains that is sized to releasably hold the catheter tip without inducing deformation in the catheter tip.

Protective portion 220 includes a protective well 221. The protective well may be a recessed area that is sized to suspend a distal portion of a catheter within the well. The catheter portion, for example a portion bearing a coated stent, is protected by being held suspended in air such that it does not contact the catheter packaging device. The suspended portion of the catheter system may be fully enclosed, as shown in FIG. 2, or may be partially enclosed. If the suspended portion is partially enclosed, the extent of enclosure should be sufficient to protect the suspended portion of the catheter system from contact with its surroundings during shipment and storage.

Catheter shaft holding portion 230 is designed to releasably hold a portion of a catheter shaft that is proximal and adjacent to the protected portion. Catheter shaft holding portion 230 may include one or more support members 231. Each support member may include an elongate channel 232 into which the catheter shaft portion is placed. The channel or channels may be designed such that, when the two separable sections of the device are combined, an opening remains that is sized to releasably hold the catheter shaft without inducing deformation in the catheter shaft.

Latching mechanisms 213 and 233 may be designed to releasably hold the two separable sections of the device together. The latching mechanism may be integral with support members 211 and 231. Those skilled in the art will appreciate that numerous locking mechanism designs are possible.

Device 200 may be fabricated from one or more suitable materials that can be conventionally formed and processed, for example polypropylene, polyethylene, a nylon/polyethylene blend, or polytetrafluoroethylene (PTFE). Such materials may minimize exchange of chemical components between the catheter system and the device during shipment and storage. That is, such materials may be nonreactive with a therapeutic agent carried in a stent coating or with other desirable coating materials, thus reducing or eliminating the risk of a therapeutic agent or other coating component migrating out of the coating and into the device material, or of a component of the device material migrating into the therapeutic agent or other coating material. Device 200 may be fabricated using one or more methods such as blow molding or injection molding.

Figure 3:
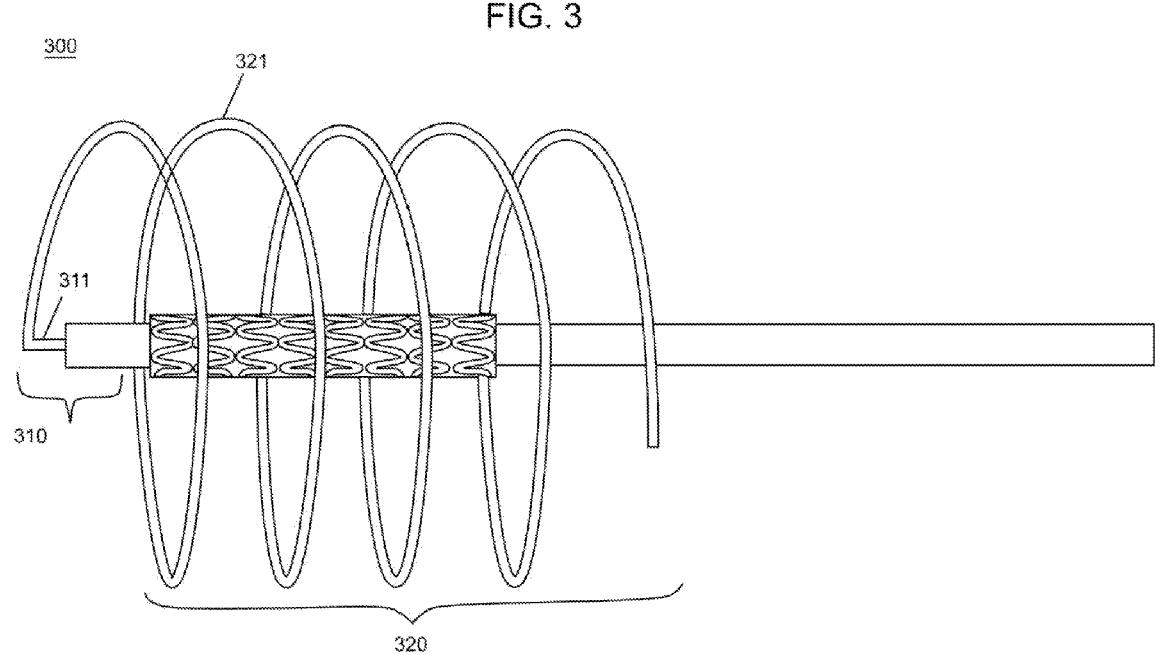
FIG. 3 is an illustration of another embodiment of a device for protecting a distal portion of a catheter system during shipment and storage, in accordance with the present invention.

Yet another embodiment of the device, in accordance with the present invention, is illustrated in FIG. 3 at 300. Device 300 includes a catheter tip holding portion 310 and a protective portion 320.

Catheter tip holding portion 310 may comprise a stylet 311. The stylet may be inserted into the catheter tip, thereby holding the device in place.

Protective portion 320 may comprise a single elongate member 321. The elongate member may be helical, forming a cage-like structure around a distal portion of a catheter system. The protected portion may bear a coated stent. The inner diameter of protective portion 320 should be larger than the outer diameter of the stent, thus reducing or eliminating contact of the stent with the device and with any other materials used to package the catheter system.

The elongate member 321 may be integral with the stylet 311. Alternatively, the device may be designed in such a way as to allow the elongate member and stylet to clip apart, thus reducing the risk of the protected portion of the catheter being damaged during removal of the device.

Device 300 may be fabricated using, for example, stainless steel wire. Such wire may be nonreactive with a therapeutic agent carried in a stent coating and with other desirable coating materials, thus reducing or eliminating the risk of a therapeutic agent or other coating component migrating out of the coating and into the device material, or of a component of the device material migrating into the therapeutic agent or other coating material.

In practice, a distal portion of a catheter system bearing a coated stent may be at least partially enclosed within the device. The catheter system with the attached device may then be inserted into a packaging hoop. The device may be curved to facilitate insertion of the device and catheter into the packaging hoop. The device may prevent or reduce contact between the coated stent and the hoop wall, both during insertion of the catheter system into the packaging hoop and during storage of the catheter system. The coated stent is thereby protected from physical damage and from the risk that extended contact of the coating with packaging materials may result in a coating component migrating out of the coating and into the packaging material or of a packaging material component migrating into the coating.

The described embodiments are intended to be used in conjunction with a catheter bearing a coated stent. However, it is anticipated that the present invention may be used to protect a distal portion of a catheter bearing a noncoated stent, a balloon, or any structure in need of protection.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

The invention claimed is:

1. A catheter shipping and storage system for protecting a distal portion of a catheter, comprising:
   a catheter system; and
   a protection device comprising:
      a detachable catheter tip holding portion to releasably hold a catheter tip;
      a protective portion operably connected to the catheter tip holding portion, wherein the protective portion at least partially encloses a distal portion of the catheter system that is proximal to and adjacent the catheter tip within the device such that the distal portion is protected during shipment and storage; and
      a detachable catheter shaft holding portion operably connected to the protective portion, wherein the catheter shaft holding portion releasably holds a portion of a catheter shaft that is proximal to and adjacent to the protected portion of the catheter system, and wherein the detachable catheter tip holding portion suspends the distal portion of the catheter within the protective portion, and wherein the catheter system is removed by detaching the catheter shaft holding portion from the catheter shaft and detaching the catheter tip from the catheter tip holding portion.

2. The system of claim 1 wherein the protective portion at least partially encloses a coated stent disposed upon the distal portion of the catheter system.

3. The system of claim 1 wherein suspension of the distal portion of the catheter system provides minimal contact of the protection device with the catheter system.

4. The system of claim 1 wherein the catheter tip holding portion comprises an opening in the protection device into which a catheter tip is inserted.

5. The system of claim 4 wherein the opening in the protection device includes a material to aid in holding the catheter tip.

6. The system of claim 4 wherein the protective portion includes at least two elongate members extending from the catheter tip holding portion.

7. The system of claim 6 wherein the catheter shaft holding portion comprises structures extending from the at least two elongate members.

8. The system of claim 7 wherein the structures extending from the at least two elongate members releasably interlock to hold the catheter shaft.

9. The system of claim 7 wherein the protection device is fabricated using one or more materials selected from a group consisting of polypropylene, polyethylene, a nylon/polyethylene blend, polytetrafluoroethylene (PTFE), a metal, and a suitable formable material that minimizes exchange of chemical components between the catheter system and the device during shipment and storage.

10. The system of claim 7 wherein the protection device is fabricated using one or more methods selected from a group consisting of blow molding, injection molding, a suitable molding method, stamping, machining, and wire forming.

11. The system of claim 1 wherein the protection device comprises at least two separable sections.

12. The system of claim 11 wherein the protection device further comprises:
   at least one latching mechanism;
   a protective well; and
   a first support member.

13. The system of claim 12 further comprising:
   a second support member.

14. The system of claim 12 wherein the at least one latching mechanism releasably holds the two separable sections of the protection device together.

15. The system of claim 12 wherein the first support member comprises the catheter tip holding portion of the protection device.

16. The system of claim 13 wherein the second support member comprises the catheter shaft holding portion of the protection device.

17. The system of claim 15 wherein the first support member includes an elongate channel into which the catheter tip is placed.

18. The system of claim 16 wherein the second support member includes an elongate channel into which the catheter shaft portion is placed.

19. The system of claim 1 wherein the shape of the protection device is arcuate to facilitate insertion into a packaging hoop.

20. The system of claim 11 wherein the protection device is fabricated using one or more materials selected from a group consisting of polypropylene, polyethylene, a nylon/polyethylene blend, polytetrafluoroethylene (PTFE), and a suitable formable material that minimizes exchange of chemical components between the catheter system and the device during shipment and storage.

21. The system of claim 11 wherein the protection device is fabricated using one or more methods selected from a group consisting of blow molding, injection molding, a combination of blow molding and injection molding, and a suitable molding method.

22. A catheter shipping and storage system for protecting a distal portion of a catheter, comprising:
- a catheter having a catheter tip and a distal portion positioned proximal to the catheter tip; and
- a catheter tip protection device having a catheter tip holding portion and a protective portion,
- wherein the catheter tip holding portion releasably holds the catheter tip; and the protective portion is operably connected to the catheter tip holding portion,
- wherein the catheter tip holding portion suspends the distal portion of the catheter and the protective portion at least partially encloses the distal portion of the catheter system within the device such that the distal portion is protected during shipment and storage, and
- wherein the catheter tip holding portion comprises a stylet.

23. The system of claim 22 wherein the protective portion comprises at least one elongate member.

24. The system of claim 22 wherein the elongate member is helical.

25. The system of claim 22 wherein the elongate member is integral with the catheter tip holding portion.

26. The system of claim 23 wherein the catheter tip protection device comprises a stainless steel wire.

* * * * *